United States Patent [19]

Griswold

[11] Patent Number: 5,091,440
[45] Date of Patent: Feb. 25, 1992

[54] ACRYLATE- OR METHACRYLATE-FUNCTIONAL ORGANOPOLYSILOXANES

[75] Inventor: Roy M. Griswold, Tulsa, Okla.

[73] Assignee: Wacker Silicones Corporation, Adrian, Mich.

[21] Appl. No.: 447,758

[22] Filed: Dec. 8, 1989

[51] Int. Cl.⁵ .............................................. C08F 2/46
[52] U.S. Cl. ...................................... 522/99; 522/172;
528/21; 528/24; 528/25; 528/26; 528/29;
528/32
[58] Field of Search ..................... 528/25, 26, 29, 32,
528/24, 21; 522/99, 172

[56] References Cited

U.S. PATENT DOCUMENTS

| | | | |
|---|---|---|---|
| 4,439,291 | 3/1984 | Irving et al. | 522/100 |
| 4,810,731 | 3/1989 | Hida et al. | 528/24 |
| 5,019,644 | 5/1991 | Cavezzan et al. | 528/29 |

*Primary Examiner*—Melvyn I. Marquis

[57] ABSTRACT

Radiation polymerizable acrylate- or methacrylate-functional organo-polysiloxanes having the structural formula

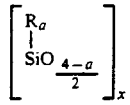

wherein R is a radical selected from the group consisting of monovalent hydrocarbon radicals having from 1 to 20 carbon atoms, substituted monovalent hydrocarbon radicals having from 1 to 20 carbon atoms, monovalent hydrocarbonoxy radicals having from 1 to 20 carbon atoms and a radical of the formula:

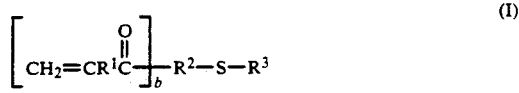

in which at least one R is a radical of formula (I), $R^1$ is hydrogen or a methyl radical, $R^2$ is selected from the group consisting of a multivalent hydrocarbonoxy radical and a multivalent hydrocarbonoxy radical containing non-terminal atoms selected from the group consisting of oxygen, sulphur and nitrogen atoms, $R^3$ is a divalent hydrocarbon radical or a divalent hydrocarbonoxy radical, a is a number having an average value of from 0.7 to 2.6, b is a number of from 1 to 5, and x is a number from 2 to 1000.

The acrylate- or methacrylate-functional organopolysiloxanes are combined with a photosensitizer and/or a peroxide and cured by radiation and/or heat. High energy electrons may be used in lieu of a photosensitizer or peroxide to cure these compositions.

17 Claims, No Drawings

ACRYLATE- OR METHACRYLATE-FUNCTIONAL ORGANOPOLYSILOXANES

BACKGROUND OF THE INVENTION

Radiation polymerizable acrylate- and methylacrylate-functional polysiloxanes have been described in U.S. Pat. No. 4,306,050 to Koepner. The patentee describes a process in which organopolysiloxanes having chlorine atoms attached to silicon atoms are reacted with pentaerythritol triacrylate or pentaerythritol trimethacrylate. The compositions prepared by this process, however, have the acrylate group linked to the silicon atom by a carbon-oxygen bond, thereby rendering the compositions hydrolytically unstable.

U.S. Pat. No. 3,878,263 to Martin describes acrylate functional polysiloxanes wherein the acrylate functional group is bonded to the silicon atom by means of a hydrolytically stable carbon-silicon bond. However, these acrylate functional polysiloxanes cure slowly when radiated with actinic radiation.

U.S. Pat. No. 4,201,808 to Cully describes acrylate functional polysiloxanes wherein the degree of acrylation is increased by having the acrylate groups linked to a silicon atoms by means of carbon-silicon linkages as well as silicon-oxygen-carbon linkages, thereby enhancing the reactivity of the composition when irradiated with actinic radiation. However, these compositions are hydrolytically unstable.

U.S. Pat. Nos. 4,606,933 and 4,762,887 to Griswold et al describe acrylate-functional polysiloxanes in which the acrylate containing group is bonded to a silicon atom by a carbon-nitrogen bond. However, it is difficult to prevent chain extension in these compositions, often resulting in a yield of highly viscous materials.

OBJECTS OF THE INVENTION

It is an object of the invention to provide novel acrylate-functional polysiloxanes. Another object of the invention is to provide novel acrylate-functional polysiloxanes that may be derived from polyhydric functional organopolysiloxanes. Still another object of the invention to provide novel acrylate-functional polysiloxanes in which some of the silicon atoms contain more than one acrylate group per molecule. A further object of the invention is to provide acrylate-functional polysiloxanes that are reactive under radiation conditions in the presence of oxygen. A further object of the invention is to provide acrylate-functional polysiloxanes in which the acrylate containing group is bonded to the silicon atom by a carbon-sulphur bond. A further object of the invention is to provide acrylate-functional polysiloxanes which are hydrolytically stable. A still further object of the invention is to provide a process for preparing acrylate-functional polysiloxanes having viscosities acceptable for gravure or multi-roll applied coatings.

SUMMARY OF THE INVENTION

The foregoing objects and others which will become apparent from the following description are accomplished, in accordance with this invention, generally speaking, by providing acrylate-functional organopolysiloxanes having the general formula;

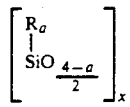

where R is a radical selected from the group consisting of monovalent hydrocarbon radicals having from 1 to 20 carbon atoms, substituted monovalent hydrocarbon radicals having from 1 to 20 carbon atoms, monovalent hydrocarbonoxy radicals having from 1 to 20 carbons and a radical of the formula

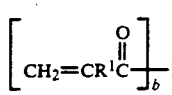

in which at least one R is a radical of formula (I), $R^1$ is hydrogen or a methyl radical, $R^2$ is selected from the group consisting of a multivalent hydrocarbonoxy radical, and a multivalent hydrocarbonoxy radical containing non-terminal atoms selected from the group consisting of oxygen, sulphur and nitrogen atoms, $R^3$ is a divalent hydrocarbon radical or a divalent hydrocarbonoxy radical, a is a number having an average value of from 0.7 to 2.6, b is a number of from 1 to 5, and x is a number of from 2 to 1000.

The acrylate- or methacrylate-functional organopolysiloxanes are combined with a photosensitizer and/or a peroxide and cured by actinic radiation and/or heat. High energy electrons may be used in lieu of the photosensitizer and/or peroxide to cure these compositions.

DETAILED DESCRIPTION OF THE INVENTION

In the acrylate- or methacrylate-functional organopolysiloxanes having the general formula

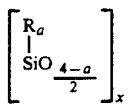

R is selected from the group consisting of monovalent hydrocarbon radicals having from 1 to 20 carbon atoms, substituted monovalent hydrocarbon radicals having from 1 to 20 carbon, monovalent hydrocarbonoxy radicals having from 1 to 20 carbon atoms and a radical having the formula

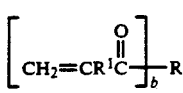

in which at least one R is a radical of formula (I), $R^1$, $R^2$, $R^3$, a, b, and x are the same as those above.

Examples of monovalent hydrocarbon radicals represented by R having from 1 to 20 carbon atoms are alkyl radicals such as methyl, ethyl, propyl, butyl, hexyl, octyl, dodecyl, octadecyl and eicosyl radicals; aryl radicals such as phenyl, biphenyl, and naphthyl radicals; alkenyl radicals such as the vinyl and allyl radicals; cycloalkyl radicals such as cyclobutyl, cyclopentyl and cyclohexyl radicals; alkaryl radicals such as the tolyl, xylyl, and ethylphenyl radicals, and aralkyl radicals such as benzyl, alpha phenylmethyl, beta phenylethyl and alpha phenylbutyl radicals.

Examples of substituted monovalent hydrocarbon radicals represented by R are the same monovalent hydrocarbon radicals described above which have been substituted with groups selected from the group consisting of the cyano radical (—CN), an acryloxy radical

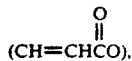
(CH=CHCO), a methylacryloxy radical

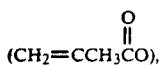
(CH$_2$=CCH$_3$CO), hydroxyl radical or a radical represented by the formula (OC$_g$H$_{2g}$)$_h$ OR$^5$, wherein R$^5$ is selected from the group consisting of a monovalent hydrocarbon radical having from 1 to 20 carbon atoms, an acryloxy radical

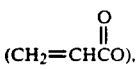
(CH$_2$=CHCO), a methacryloxy radical (CH$_2$=CCH$_3$CO) or an acetyl radical radical

(CH$_3$C), is a number of from 2 to 4 and h is a number of from 1 to 300.

The monovalent hydrocarbon radical represented by R$^5$ may be the same as those represented by R.

Examples of monovalent hydrocarbonoxy radicals represented by R having from 1 to 20 carbon atoms are those having the formula (OR$^4$), wherein R$^4$ is a monovalent hydrocarbon radical. The examples of the monovalent hydrocarbonoxy radicals represented by R above also applies to the R$^4$ radicals.

The R$^2$ radical is a linear or branched radical and provides sites for linking up to five acrylate or methacrylate groups. The R$^2$ radical contains carbon, hydrogen and oxygen atoms, and in addition may contain non-terminal oxygen, sulphur and/or nitrogen atoms. More specifically R$^2$ may be further represented by the formula R$^6$, where R$^6$ is represented by the radicals:

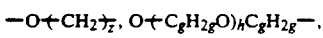

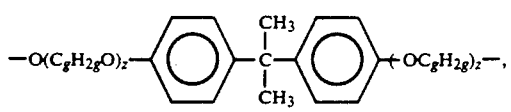

-continued

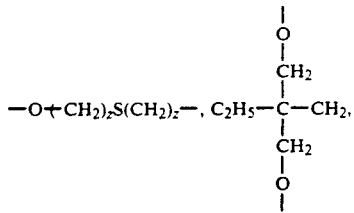

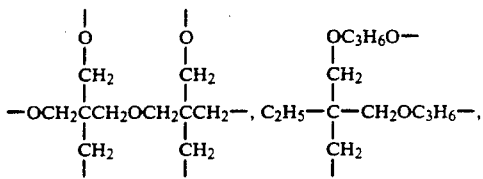

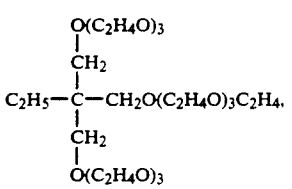

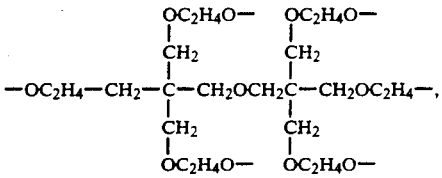

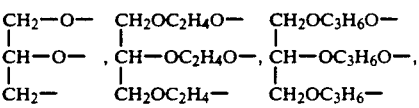

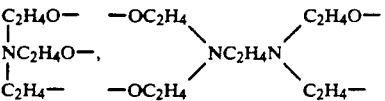

where g and h are the same as defined above and z is a number of from 1 to 300.

Examples of divalent hydrocarbon radicals represented by R$^3$ having from 2 to 20 carbon atoms are alkylene radicals such as ethylene, trimethylene, tetramethylene, hexamethylene, octamethylene and eicosamethylene radicals.

Examples of divalent hydrocarbonoxy radicals represented by R$^3$ having from 2 to 20 carbon atoms are those having the general formula C$_2$H$_4$(OC$_g$H$_{2g}$)$_h$(CH$_2$)$_j$, wherein g and h are the same as above, and j is a number of from 3 to 14.

Examples of suitable divalent hydrocarbonoxy radicals represented by R$^3$ include C$_2$H$_4$(OC$_2$H$_4$)$_{10}$OC$_3$H$_6$, C$_3$H$_6$(OC$_2$H$_4$)$_{20}$OC$_3$H$_6$, C$_2$H$_4$(OC$_3$H$_6$)$_{20}$OC$_3$H$_6$ wherein h is the same as above.

These acrylate- or methacrylate-functional organopolysiloxanes may be prepared by (1) reacting alkylene sulfides with polyhydric alcohols or reacting hydrogen sulfide with polyhydric alcohols using alumina as the catalyst, or reacting a fluoropyridinum salt and sodium N,N-dimethylthiocarbamate with polyhydric alcohols, or reacting a metal sulfide with epoxy functional polyhydric alcohols, to form mercapto-functional polyhydric alcohols, then (2) reacting the resultant mercapto functional polyhydric alcohols with vinyl or allyl containing organopolysiloxanes to form carbinol functional organopolysiloxanes and thereafter (3) esterifying or transesterifying the carbinol functional organopolysiloxanes obtained from reaction (2) with acrylic acid, methacrylic acid or esters thereof.

Examples of sulfides which may be employed in step (1) of the process are alkylene sulfides such as ethylene sulfide and propylene sulfide. Examples of metal sulfides which may be employed in step (1) of the process are sodium sulfide and potassium sulfide.

Examples of suitable polyhydric alcohols which may be employed in step (1) of the process are triols and higher polyhydric alcohols such as trimethylolpropane, glycerol, pentaerythritol, dipentaerythritol ether, triethanol amine, tetraethanol ethylenediamine, sorbitol, polyhydric polyvinyl alcohols, and polyhydric alcohols which were previously reacted to incorporate polyethylene oxide or polypropylene oxide groups therein.

The vinyl containing polysiloxanes which are employed in step (2) of the process are the same vinyl functional polysiloxanes known in the art. In general, the vinyl silanes and cyclic siloxanes are preferably reacted with the mercapto-functional polyhydric alcohols, although vinyl silanes and silanol functional siloxanes may also be used.

The reaction of vinyl functional silanes and cyclic siloxanes or silanol functional siloxanes with the mercaptofunctional polyhydric alcohols may be acid or base catalyzed and is preferably carried out at a temperature of from 50 to 200° C. and more preferably from 75° to 150° C., and more preferably from 75° to 125° C. Suitable catalysts include sulfuric acid, sulfuric acid activated clays (available from Filtrol Corporation), hydrochloric acid, hydrochloric acid treated clays, potassium hydroxide and sodium hydroxide.

Examples of suitable vinyl silanes are vinylalkoxysilanes such as vinyltrimethoxysilane, methyl vinyldimethoxysilane, dimethylvinylmethoxysilane, dimethyltriethoxysilane, methylvinyldiethoxsilane, dimethylvinylethoxysilane, vinylethyldiethoxysilane, vinyltris(2methoxyethoxy)silane; vinylacetoxysilanes such as vinylmethyldiacetoxysilane, vinylethyldiacetoxysilane and vinyl triacetoxysilane; allyalkoxysilanes such as allyltrimethyoxysilane, allylmethyldimethoxysilane, and allyltriethoxysilane; divinylalkoxysilanes and divinylacyloxysilanes such as divinyldimethoxysilane, divinyldiethoxysilane and divinyldiacetoxysilane and divinyldiacetoxysilane, diallylalkoxysilanes such as diallyldimethoxysilane, diallyldiethoxysilane and diallylacyloxysilanes such as diallylacetoxysilane, diallyldiacetoxysilane as well as other ethyleneically unsaturated silane monomers such as divinyltetramethylenedisiloxane and divinyltetraethyldisiloxane may be employed It is to be understood that mixtures of vinyl type silanes also give satisfactory results.

Examples of suitable cyclic siloxanes and silanol functional siloxanes which may be employed are represented by the respective formulas:

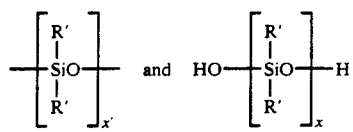

where R' is selected from the group consisting of monovalent hydrocarbon radicals having from 1 to 20 carbon atoms, substituted monovalent hydrocarbon radicals having from 1 to 20 carbon atoms and monovalent hydrocarbonoxy radicals having from 1 to 20 carbon atoms and x' is a number of from 3 to 10 and x is the same as above.

The specific examples cited for the R radicals also apply to the R' radicals.

The carbinol-functional organopolysiloxanes are prepared in step (2) of the process by reacting the mercapto-functional polyhydric alcohols with the vinyl containing organopolysiloxanes. In general the reaction is accomplished in an organic solvent in the presence of a free radical catalyst at a temperature of from 70° to 200° C. preferably from 70° to 125° C. and more preferably from 70° to 90° C. Actinic radiation may be used in conjunction with heating.

Examples of suitable solvents are alcohols, ketones, esters, and aromatic hydrocarbons or mixtures thereof. The solvents may be alcohols such as ethanol, propanol, isopropanol and butanol; ether alcohols such as propylene glycol monoethylether, dipropanol glycol monoethylether; ketones such as methyl ethyl ketone, methyl-nbutyl ketone, and methyl isobutyl ketone; esters such as butyl acetate; and aromatic hydrocarbons such as benzene, toluene, xylene and naphtha.

Examples of suitable free radical catalysts which may be employed in preparing the carbinol-functional organopolysiloxanes are organic peroxides and/or photosensitizers. Illustrative of the organic peroxides are benzoyl peroxide, dibenzoyl peroxide, ditertiary butyl peroxide, tertiary butyl benzoyl peroxide, cumene hydroperoxide, lauroyl peroxide, alpha, alpha-bis(tertiarybutylperoxy) diisopropylbenzene, 2,5,-bis(tertiarybutylperoxy)-2,5,dimethylhexane, tertiary butylperbenzoate, azobisisobutyronitrile and 2,2'-azobis(2,4-dimethylvaleronitrile).

Suitable photosensitizers include benzophenone, xanthone, thioxanone, 2-chlorothioxanone, benzoin isopropyl ether, benzoquinone, 1-chloranthroquinone, paradiacetyl benzene, 9,10-dichloroanthracene, 4,4-dichlorobenzophenone, 1,3-diphenyl-2-propane, 1,4-naphthyl phenyl ketone, and 2,3-pentanedione. Any combination of peroxides and photosensitizers will give satisfactory results.

The amount of free radical initiator, peroxide and/or photosensitizer generally used ranges from about 0.1 mole to 1 mole per mole of mercaptofunctional polyhydric alcohol.

The resulting carbinol-functional polysiloxanes are either esterified or transesterified in step (3) of the process by methods familiar to those skilled in the art. The esterification or transesterification is preferably conducted using an azeotropic solvent or solvents. However other suitable solvents may be used.

Examples of acrylic and methacrylic compounds which may be employed in the reaction with the carbinol-functional polysiloxanes are acrylic acid and methacrylic acid as well as acrylates and methacrylates.

Examples of suitable acrylates which may be employed are methylacrylate, ethylacrylate, propylacrylate, butylacrylate, hexylacrylate, octylacrylate, decylacrylate, and the corresponding methacrylates.

The reaction is carried out at a temperature of from 90° C. to 135° C., using an inhibitor to prevent prepolymerization of the acrylate or methacrylate groups and a suitable catalyst. If azeotropic solvents are not used, the reaction may be carried out using dehydrating agents such as molecular sieves, or distillation may be employed. When the products are transesterified the acrylic or methacrylic ester may also be used as a co-distillation solvent. Suitable solvents for azeotropic distillation include alkane solvents such as heptane, and cyclohexane; and aromatic solvents such as benzene, toluene and xylene.

Examples of inhibitors that will prevent premature polymerization of acrylate or methacrylate groups include hydroquinone, monomethyl ether of hydroquinone, phenothiazene and di-tertiary butyl para-cresol. The inhibitor is added in a quantity equal to from 50 to 1000 parts per million, preferably from 100 to 500 parts per million based on the carbinol functional polysiloxanes.

Examples of suitable catalysts which may be employed in the esterification or transesterification reaction include sulfuric acid, para-toluene sulfonic acid, ethylorthotitinate and alumina. The catalyst is added in an amount preferably of from 0.1 to 0.2 weight percent based on the weight of the carbinol functional polysiloxanes.

The acrylate-functional polysiloxanes of this invention may be polymerized by exposing them to a radiation source. Examples of radiation sources which may be employed are ionizing or actinic non-ionizing radiation such as electron beam, ultraviolet light, x-ray, gamma-ray and bet-ray.

When the acrylate-functional polysiloxanes are to be cured by exposure to nonionizing radiation source, such as ultraviolet light, then it is preferred that a photosensitizer be incorporated in the acrylate-functional polysiloxanes.

Photosensitizers which may be employed are benzophenone, xanthone, thioxanthone, 2-chlorothioxanthone, benzoinisopropyl ether, benzoquinone, 1-chloroanthraquinone, p-diacetylbenzene, 9,10-dichloroanthracene, 4,4-dichloroanthraquinone, 1,3-diphenyl-2-propane, 1,4-naphthylphenyl ketone, 2,3-pentanedione, 1-hydroxycyclohexylphenyl ketone, mixtures of benzophenone and tertiary amines, such as N,N-dimethylethanolamine and diazo compounds which dissociate into free radicals, such as N,N-azobisisobutyronitrile.

The photosensitizers are preferably used in an amount up to about 20 weight percent, based on the weight of the acrylate-functional polysiloxanes. More preferably, the photosensitizer is present in an amount of from about 0.5 to about 10 weight percent, based on the weight of the acrylate-functional polysiloxanes.

The radiation polymerizable acrylate-functional polysiloxanes of this invention may be stabilized against a premature polymerization during storage by the addition of a conventional polymerization inhibitor such as hydroquinone, monomethyl ether of hydroquinone, phenothiazine and di-t-butyl paracresol in concentrations on the order of about 0.1 weight percent or less based on the weight of the radiation curable acrylate-functional polysiloxanes.

Polymerization may be carried out in an air atmosphere or in an inert atmosphere such a argon or nitrogen. The time required to polymerize a coating containing the acrylate- or methacrylate-functional polysiloxanes varies with such factors as the particular composition used, type and wavelength of radiation, energy flux, concentration of the photosensitizer and the thickness of the coating; however, it is generally relatively short, that is, less than about 10 seconds.

The acrylate-functional polysiloxanes of this invention may also be thermally polymerized or they may be polymerized in the presence of a free radical initiator, such as an organic peroxide. When an organic peroxide is employed, it is preferably employed in an amount of from about 0.1 to 10 weight percent based on the weight of the acrylate-functional polysiloxanes.

Examples of suitable organic peroxides are benzoyl peroxide, dibenzoyl peroxide, di-t-butyl peroxide, t-butylbenzoyl peroxide, cumene hydroperoxide, dicumyl peroxide, lauroyl peroxide, alpha, alpha'-bis(t-butylperoxy)diisopropylbenzene, 2,5-bis(t-butylperoxy)-2,5-dimethylhexane and t-butyl perbenzoate.

In addition to the acrylate-functional polysiloxanes, the compositions of this invention may also contain other additives such as diluents, flow control agents, levelling agents, inhibitors, pigments and the like. Examples of reactive diluents which may be added to the acrylatefunctional polysiloxanes of this invention are ethyl acrylate, n-amyl acrylate, benzyl acrylate, cyclohexyl acrylate, 2-(N-methylcarbamoyloxy)ethylacrylate, diethylaminoethyl acrylate, 2-ethoxyethyl acrylate, n-lauryl acrylate, n-octyl acrylate, octadecyl acrylate, vinyl acetate, and N-vinylpyrrolidone and others. The corresponding methacrylate esters may be used; however, they are less desirable. If desired, a low viscosity siloxane fluid having a single acrylate or methacrylate group bonded thereto may be employed as a diluent. The diluent can be employed in an amount of from about 0.001 to about 99 weight percent based on the weight of the acrylate-functional polysiloxane and more preferably in an amount of from about 10 to 95 weight percent based on the weight of the acrylate-functional polysiloxane.

The compositions of this invention containing acrylate-functional polysiloxanes may be applied to various substrates, such as paper, wood, glass, polycarbonates, polyesters, polymethylmethacrylates and metal surfaces such as aluminum, steel, copper and brass and then polymerized in the presence of a radiation source or heat.

The compositions of this invention may be used to form clear and pigmented coatings on paper substrates and pigmented coatings on metal and glass substrates, as well as coatings for fiber glass, as overprint varnishes.

The invention is further illustrated by the following example in which all parts are by weight unless otherwise specified.

EXAMPLE

A mercaptofunctional polyhydric alcohol was prepared by heating 33.0 parts of ethylene sulfide, 74.8 parts of pentaerythritol, 20 parts of 1,1,1-trichloroethane and 0.1 part of alumina at a temperature of from 75° to 85° C. for 16 hours. The product was cooled and filtered. About 21.7 parts of the resultant product was reacted with 200.0 parts of a vinyl containing polydimethylsiloxane having a viscosity of 4000 mPa.s at 25° C. and a vinyl to Si ratio of 2 to 60 in the presence of 0.3 parts of t-butylperbenzoate at a temperature of from 75° to 85° C. for 16 hours to form a carbinol-functional polydimethylsiloxane. The carbinol-functional polydimethylsiloxane thus prepared was devolatilized at 175° C. under a vacuum of 0.1 torr for 1 hour.

To 150 parts of the carbinol-functional polysiloxane was added, 14.6 parts of acrylic acid, 50 parts of toluene, 0.04 part of p-methoxyphenol and 0.1 part of p-toluene sulfonic acid. The reaction mixture was refluxed at 130° C. while collecting the aqueous volatiles in a moisture trap. A total of 2.1 g of aqueous volatiles were collected and discarded. The resultant product was neutralized with 0.1 part of magnesium hydroxide and filtered. The product was devolatilized under a vacuum of 0.1 torr and at a temperature of 130° C. for 1 hour. The resultant product was identified as being an acrylate-functional polydimethylsiloxane.

The acrylate-functional polydimethysiloxane prepared above, was mixed with 4 percent by weight of 1-hydroxycyclohexylphenyl ketone (available as Irgacure® 184 from Ciba-Geigy Corporation) and cured under a 200 watt/inch ultra violet processor at 50 feet/minute to give a tack free elastic film.

Obviously many modifications and variations of the process may be made without departing from the scope of the invention.

What is claimed is:

1. Acrylate- or methacrylate-functional organopolysiloxane compositions containing an organopolysiloxane of the formula

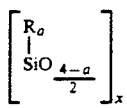

wherein R is a radical selected from the group consisting of monovalent hydrocarbon radicals having from 1 to 20 carbon atoms, substituted monovalent hydrocarbon radicals having from 1 to 20 carbon atoms, monovalent hydrocarbonoxy radicals having from 1 to 20 carbon atoms and a radical of the formula

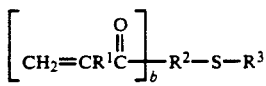 (I)

wherein at least one R is a radical of formula (I), $R^1$ is selected from the group consisting of hydrogen and a methyl radical, $R^2$ is selected from the group consisting of a multivalent hydrocarbonoxy radical and a multivalent hydrocarbonoxy radical containing non-terminal atoms selected from the group consisting of oxygen, and nitrogen atoms, $R^3$ is selected from the group consisting of a divalent hydrocarbon radical and a divalent hydrocarbonoxy radical, a is a number having an average value of from 0.7 to 2.6, b is a number of from 1 to 5, and x is a number of from 2 to 200; said acrylate- or methacrylate-functional organopolysiloxane compositions are obtained by reacting a mercapto-functional compound selected from the group consisting of mercaptofunctional monohydric alcohols, mercapto-functional polyhydric alcohols, mercapto-functional monohydric alcohols containing non-terminal atoms selected from the group consisting of oxygen and nitrogen atoms and mercapto-functional polyhydric alcohols containing non-terminal atoms selected from the group consisting of oxygen and nitrogen atoms with organopolysiloxanes containing vinyl or allyl groups and thereafter the result product is reacted with an acid or ester thereof selected from the group consisting of an acrylic and methacrylic acid in the presence of a free radical initiator.

2. The composition of claim 1, wherein the $R^2$ radical is a multivalent hydrocarbonoxy radical.

3. The composition of claim 1, wherein the $R^2$ radical is a multivalent hydrocarbonoxy radical containing non-terminal atoms selected from the group consisting of oxygen and nitrogen atoms.

4. The composition of claim 1, wherein the $R^3$ radical is a divalent hydrocarbonoxy radical having from 2 to 20 carbon atoms.

5. The composition of claim 1, wherein the $R^3$ radical is a divalent hydrocarbonoxy radical having from 2 to 20 carbon atoms.

6. The composition of claim 1, wherein the $R^1$ radical is hydrogen.

7. The composition of claim 1, wherein the R radical is a substituted monovalent hydrocarbon raical in which substituted groups are selected from the group consisting of a cyano radical, acryloxy radical, methacryloxy radical, hydroxyl radical and a radical of the formula

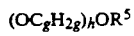

where $R^5$ is selected from the group consisting of a monovalent hydrocarbon radical having from 1 to 20 carbon atoms, an acryloxy radical, a methacryloxy radical and an acetyl radical, g is a number of from 2 to 4 and h is a number of from 1 too 300.

8. The composition of claim 1, wherein the R radical is a vinyl radical.

9. The composition of claim 1, wherein the R radical is an allryl radical.

10. The composition of claim 1, wherein the composition contains a photosensitizer.

11. The composition of claim 1, wherein the composition contains an organic peroxide.

12. The composition of claim 10, wherein the composition also contains an organic peroxide.

13. The composition of claim 10, wherein the photosensitizer is present in an amount of from about 0.5 to about 20 percent by weight based on the weight of the acrylate- or methacrylate-functional organopolysiloxane.

14. The composition of claim 11, wherein the organic peroxide is present in an amount of from about 0.1 to about 10 percent by weight based on the weight of the acrylate- or methacrylate-functional organopolysiloxane.

15. A process for preparing acrylate- or methacrylate-functional organopolysiloxane compositions which comprises reacting (1) a sulfide selected from the group consisting of an alkylene sulfide and hydrogen sulfide with a polyhydric alcohol in the presence of an alumina catalyst to form a mercapto-functional polyhydric alcohol, (2) reacting the resultant mercapto-functional polyhydric alcohol with an organopolysiloxane having aliphatic unsaturation to form a carbinol-functional organopolysiloxane and thereafter (3) reacting the resultant carbinol-functional organopolysiloxane with a compound selected from the group consisting of acrylic acid, methacrylic acid and esters thereof.

16. The process of claim 15, wherein the mercaptofunctional polyhydric alcohol is prepared by reacting a metal sulfide with an epoxy-functional polyhydric alcohol.

17. The process of claim 15, wherein the mercaptofunctional polyhydric alcohol is prepared by reacting a fluoropyridinum salt and sodium N,N-dimethylthiocarbamate with a polyhydric alcohol.

* * * * *